United States Patent [19]
Gerber

[11] Patent Number: 6,055,456
[45] Date of Patent: Apr. 25, 2000

[54] SINGLE AND MULTI-POLAR IMPLANTABLE LEAD FOR SACRAL NERVE ELECTRICAL STIMULATION

[75] Inventor: Martin Theodore Gerber, Maple Grove, Minn.

[73] Assignee: Medtronic, Inc., Minneapolis, Minn.

[21] Appl. No.: 09/301,937

[22] Filed: Apr. 29, 1999

[51] Int. Cl.$^7$ ...................................................... A61N 1/05
[52] U.S. Cl. .............................................................. 607/117
[58] Field of Search ........................... 607/116–119, 122, 607/125, 133

[56] References Cited

U.S. PATENT DOCUMENTS

| | | | |
|---|---|---|---|
| 3,769,984 | 11/1973 | Muench | 607/122 |
| 4,355,646 | 10/1982 | Kallok et al. | 607/122 |
| 4,607,639 | 8/1986 | Tanagho et al. | |
| 4,633,889 | 1/1987 | Tallalla et al. | 607/117 |
| 4,771,779 | 9/1988 | Tanagho et al. | |
| 5,425,751 | 6/1995 | Baeton et al. | |
| 5,462,545 | 10/1995 | Wang et al. | 607/116 |
| 5,603,730 | 2/1997 | Romkee | 607/116 |
| 5,683,445 | 11/1997 | Swoyer | 607/119 |
| 5,702,437 | 12/1997 | Baudino | |
| 5,713,922 | 2/1998 | King | |

*Primary Examiner*—William E. Kamm
*Assistant Examiner*—George R. Evanisko
*Attorney, Agent, or Firm*—Banner & Witcoff, Ltd.

[57] ABSTRACT

An implantable medical lead for stimulation of the sacral nerves comprises a lead body which includes a distal end and a proximal end, and the distal end having at least one electrode contact having a length of between 0.10 and 1.50 inches extending longitudinally from the distal end toward the proximal end. The lead body at its proximal end may be coupled to a pulse generator, additional intermediate wiring, or other stimulation device. The implantable medical lead can comprise a first and second electrode contacts. The second electrode contact has a length of between 0.030 and 1.00 extending longitudinally from a point approximately 1.00 from the distal end toward the proximal end. The first and second electrode contacts do no overlap longitudinally. The implantable lead is implanted by taking the lead and implanting near the sacral nerves and then connecting to a pulse generator.

4 Claims, 3 Drawing Sheets

SINGLE AND MULTI-POLAR IMPLANTABLE LEAD FOR SACRAL NERVE ELECTRICAL STIMULATION

BACKGROUND OF THE INVENTION

1. Field of the Invention

This invention relates generally to an apparatus that allows for non-direct contact stimulation of the sacral nerves. More specifically, this invention relates to an implantable medical lead having at least one electrode contact wherein the lead is implanted near the sacral nerves for stimulation of a bundle of nerve fibers. Moreover, this invention relates to the method of implantation and anchoring of the medical lead near the sacral nerve to allow for non-direct contact stimulation.

2. Description of Related Art

Pelvic floor disorders such as, urinary incontinence, urinary urge/frequency, urinary retention, pelvic pain, bowel dysfunction (constipation, diarrhea), erectile dysfunction, are bodily functions influenced by the sacral nerves that can be treated using electrical stimulation. Specifically, urinary incontinence is the involuntary control over the bladder that is exhibited in various patients. Electrical stimulation of the sacral nerves can result in partial control over the evacuation function of the bladder and other related functions. Thus, for example, medical leads having discrete electrode contacts have been implanted on and near the sacral nerves of the human body to provide partial control for bladder incontinence. Other methods have been used to control bladder incontinence, for example, vesicostomy or an artificial sphincter implanted around the urethe. These solutions have drawbacks well known to those skilled in the art. In addition, some disease states do not have adequate medical treatments.

In one current method of treatment for incontinence using electrical stimulation, two stimulation systems are implanted and have an implantable lead with discrete electrodes positioned directly on selected sacral nerves for sphincter and bladder stimulation respectively. The leads are connected to a pulse generator wherein an electrical stimulation pulse is transmitted. The sphincter is stimulated to prevent incontinence. When it is desired to evacuate the bladder, the electrical pulse to the sphincter is closed and the electrode connected to the bladder function is stimulated. After a delay, the bladder system stimulation is discontinued and the sphincter is again stimulated. A system and method for inserting an electrical lead within a human for applying electrical stimulation to the sacral nerves for control of incontinence and other related functions is discussed in U.S. Pat. No. 4,771,779 issued to Tanagho et al., and herein is incorporated by reference.

Incontinence is primarily treated through pharmaceuticals and surgery. Many of the pharmaceuticals do not adequately resolve the issue and can cause unwanted side effects and a number of the surgical procedures have a low success rate and are not reversible. Typically, existing leads have four small discrete electrodes built into the distal end of the lead. During implantation, the physician steers the implantable pulse generator outputs to the electrodes to provide the most efficacious therapy.

Unlike other surgical procedures, sacral nerve stimulation using an implantable pulse generator is reversible by merely turning off the pulse generator. The current electrical designs used for sacral nerve stimulation are not optimized for the application. Additionally, due to the small size of the stimulation electrodes, up to 0.060 inches, physicians spend a great deal of time with the patient under a general anesthetic placing the leads. The patient is thereby exposed to the additional dangers associated with extended periods of time under a general anesthetic. The current lead design used for sacral nerve stimulation uses 4 electrodes. Each electrode has a length of 0.030 inches and are spaced by 0.030 inches. Another lead that is currently used has electrodes 0.060 inches spaced by 0.060 inches.

A problem associated with the prior art electrical stimulation to control incontinence is positioning and maintaining the discrete electrode in casual contact or in close proximity to the nerve to provide adequate stimulation of the sacral nerves. Another problem is constant or consistent stimulation. Accordingly, there remains a need in the art for an implantable electrical lead that allows for stimulation of a bundle of nerves and allows for some movement after implantation.

SUMMARY OF THE INVENTION

The present invention recognizes and provides a solution to the problems associated with implanting and maintaining electrical leads in close proximity or casual contact with discrete nerve fibers of the sacral nerves by providing a unique solution that allows implantation near the sacral nerves. Additionally, the invention provides a method of implanting a medical electrical stimulation lead for control of incontinence by stimulating a bundle of nerve fibers of the sacral nerve. Briefly, the present invention comprises a lead with at least one electrical contact extending for a length of between 0.10 and 1.50 inches.

Accordingly, an object of the present invention is to provide for a unique implantable medical electrical stimulation lead that provides adequate stimulation of the sacral nerves for control of incontinence and other pelvic floor disorders without direct contact with the sacral nerves and with less sensitivity to placement. The unique lead simplifies the implant procedure and reduces or eliminates the need to reprogram the implantable pulse generator stimulation levels or re-open the patient to move the lead.

Another object of this invention is to provide an implantation method for more rapid placement of medical electrical leads for the treatment of incontinence whereby the lead is placed near the sacral nerves. Implanting the medical electrical lead near the sacral nerves with less specificity as to location near the sacral nerves reduces the time for implantation. Currently, the implantation procedure for existing medical electrical leads stimulating the sacral nerve fibers takes approximately 20–60 minutes. The current invention allows for implantation near the sacral nerve bundle and reduces the time for implantation to approximately 5–10 minutes. The larger electrode of this invention creates a wider electric field which allows the lead to be placed in a less precise or gross manner while still providing adequate electrical stimulation to the sacral nerve.

Yet another object of this invention is to provide a medical electrical lead and method of implantation whereby the lead can allow for some movement of the lead without deteriorating the capture of the sacral nerves. Because the electrode does not need to be in direct contact with the nerve fibers and due to the large electrode area, a small amount of movement from the original implant position does not reduce the nerve capture.

A further object of this invention is to provide a medical electrical lead for stimulating the sacral nerves having a smaller than typical diameter. Providing the medical electrical lead with a smaller diameter may allow for alternate less invasive implantation techniques such as the use of a cannula. The smaller diameter medical electrical lead provides less trauma to a patient during implantation. Using this system for implantation may allow the physician to use a local anesthesia instead of a general anesthesia thus reducing the dangers inherent with the use of a general anesthetic.

The full range of objects, advantages, and features of this invention are only appreciated by a full reading of this specification and a full understanding of the invention. Therefore, to complete this specification, a detailed description of the invention and the preferred embodiments follow, after a brief description of the drawing wherein additional objects, advantages and features of the invention are disclosed.

BRIEF DESCRIPTION OF THE DRAWINGS

A preferred embodiment of the invention is illustrated in the drawings, wherein like reference numerals refer to like elements in the various views, and wherein.

In the accompanying drawings, like reference numbers are used throughout the various figures for identical structures.

DESCRIPTION OF THE PREFERRED EMBODIMENTS

Figure 1:
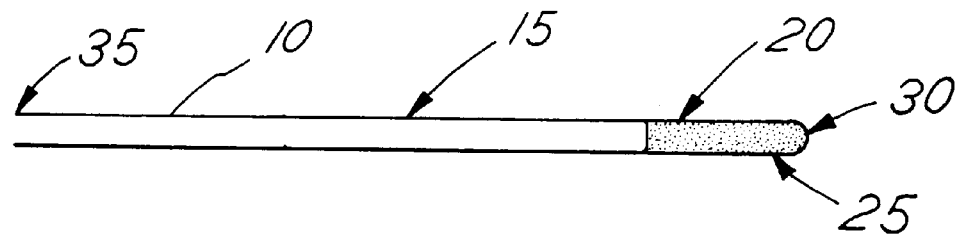
FIG. 1 is a plan view of the lead with one electrode contacts extending from the distal end.

Referring to FIG. 1, an implantable medical lead 10 that allows for non-direct contact stimulation of the sacral nerves comprises a lead body 15 having at least one electrode contact 20 and a distal end 25. The electrode contact 20 extends longitudinally for a length of between 0.10 inches and 1.50 inches from the distal end 25 toward a proximal end 35. The distal end 25 of the lead body 15 may comprise a conductive tip 30. The construction of the lead body distal end 25 may also comprise a non-conductive tip 30.

The proximal end 35 of the lead body 15 may be coupled to a pulse generator, additional intermediate wiring, or other stimulation device. An example of such a pulse generator is the Medtronic InterStim Neurostimulator Model 3023. The stimulation pulses produced by the pulse generator are carried from the pulse generator through the proximal end 35 of the lead body 15 of the present invention toward the distal end 25 having at least one electrode contact 20.

The length of the electrode contact 20 in the preferred embodiment is 0.40 inches in length. The current typical lead for stimulation of the sacral nerves includes a discrete electrode. The larger electrode contact 20 of this invention generates a larger electric field for stimulating the sacral nerve. The larger electric field makes it easier to stimulate the nerve bundle. Because this medical lead 10 does not require the specificity of location of current leads, the implantation process is simplified.

In the preferred embodiment, the electrode contact 20 is made of a solid surface material. Examples of solid surface materials are platinum, platinum-iridium, and stainless steel. The electrode contact 20 may also be made up of a coiled wire. The electrode contact material is selected based on the forming and corrosive properties of the material when subjected to the conditions within the human body.

The lead body 15 of the present invention comprises one or more conductor wire(s) within an insulating sheath. The conductor material is preferably an MP35N alloy. The lead body 15 insulation material is preferably polyurethane or silicone. Other suitable materials known to those in the art may also be used. A typical diameter of the lead body 15 is 0.050 inches but a smaller diameter is also acceptable.

Figure 2:
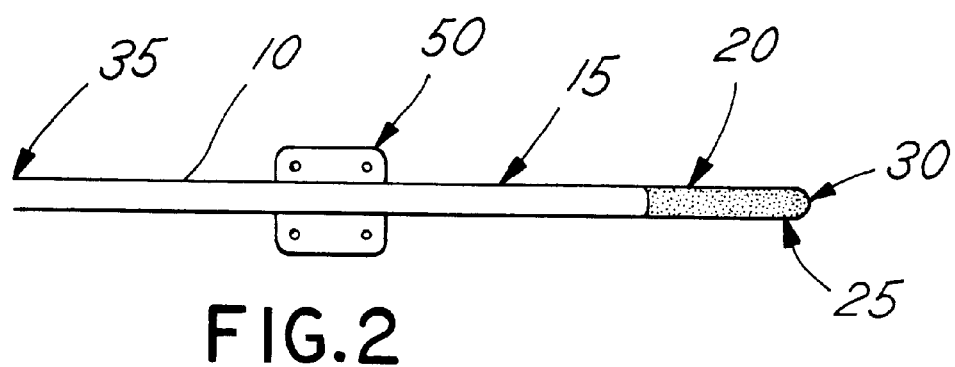
FIG. 2 is a plan view of the lead with one electrode extending from the distal end and including an anchoring mechanism.

Referring to FIG. 2, the implantable medical lead 10 of the present invention may have an anchoring mechanism 50 to fixate the medical lead 10 in the desired position. The anchoring mechanism 50 is a molded part, integral to the medical lead 10, where the physician can pass the sutures through the molded part to attach the medical lead 10 to the human anatomy. The anchoring mechanism 50 has at least one through hole, shown in FIG. 2, that allows the medical lead 10 to be inserted through the anchoring mechanism before adhering to the body. Another anchoring mechanism 50 is adapted to allow the use of a bone screw to screw to adhere the lead to the sacrum. Another anchoring mechanism 50 includes attaching an anchor to the medical lead 10 during the implantation procedure to allow the physician to suture to the anatomy. Yet another anchoring mechanism 50 is to allow the medical lead 10 to fibrose in naturally using the human body's natural reaction to a foreign body or healing. A further anchoring mechanism 50 is to use enzyme glues to provide the necessary anchoring.

Figure 3:
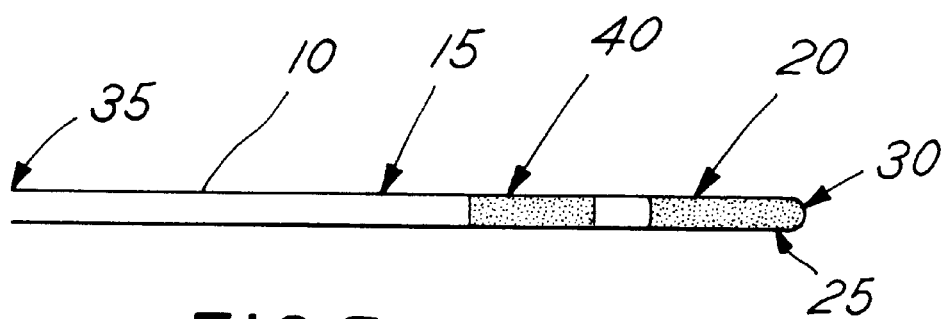
FIG. 3 is a plan view of the lead having two electrode contacts to provide for a bipolar configuration.

Turning to FIG. 3, the medical lead 10 of the present invention may have two electrode contacts 20 and 40. As above, the first electrode contact 20 is preferably 0.40 inches in length. The second electrode contact 40 is preferably 0.60 inches in length. The length of the first and the second electrode contacts 20 and 40 extend longitudinally from the distal end 25 toward the proximal end 35. The first electrode contact 20, as above in the single electrode embodiment, begins at the distal end having either a conductive or a non-conductive tip 30. The second electrode contact 40 extends for a length starting at approximately 1.00 inch from the distal end 30 toward the proximal end 35. The first electrode contact and the second electrode contact do not overlap. The second electrode contact extends from a point beyond the end of the first electrode contact toward the proximal end. The length of the second electrode contact 40 is preferably 0.60 inches but may range between 0.03 and 1.00 inches. The length of the second electrode contact 40 must be large enough that the current density is not at a level that causes damage to the tissue or that may be sensed by the patient.

As above, the first and second electrode contacts 20 and 40 can be made of a solid surface material, for example platinum, platinum-iridium, or stainless steel. The first and second electrode contacts 20 and 40 may also be constructed of a coiled wire. Another alternative embodiment of the medical lead 10 includes the first electrode contact 20 comprising a solid surface material and the second electrode contact 40 comprising a coiled wire. A coiled first electrode contact 20 may be preferred from a physiological standpoint whereas a solid second electrode may be preferred from a manufacturing perspective. The preferred embodiment will have a coiled first electrode contact 20 and a solid surface material second electrode contact 40. Where two electrodes are used, the first electrode contact 20 will be one polarity and the can of the implantable pulse generator will be the other polarity. In some instances, where the patient has pain at the implantable pulse generator site caused or increased by the stimulation, the second electrode contact 40 would be used instead of the can of the implantable pulse generator, thus eliminating the pain at the implantable pulse generator site. The first and second electrode contacts 20 and 40 are sized such the first electrode contact 20 does not longitudinally overlap with the second electrode contact 40.

Figure 4:
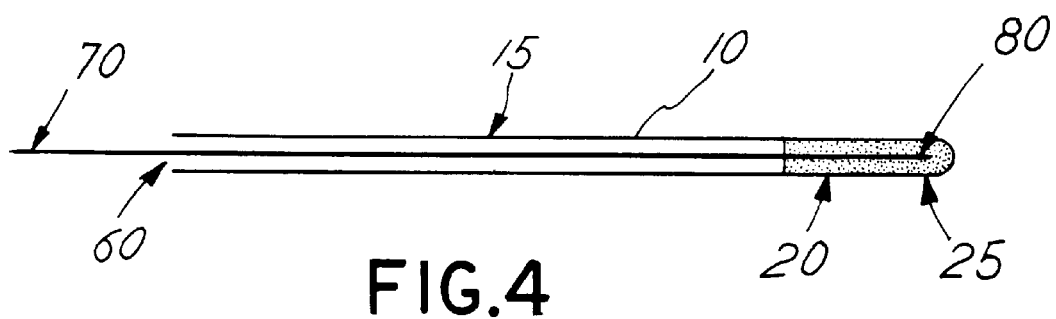
FIG. 4 is a plan view of the lead adapted to accept a stylet.

In FIG. 4, the implantable medical lead 10 may include an internal cavity 60 shaped to accept a stylet 70. The stylet 70 is inserted into the lead body internal cavity 60 prior to implantation. The stylet 70 is made of solid wire such as tungsten or stainless steel. By inserting a stylet 70 into the lead body internal cavity 60, the medical lead 10 is stiffened to provide support to the lead body 15 during implantation. Use of a medical lead 10 with a stylet 70 is particularly useful for implantation using a cannula.

Figure 5:
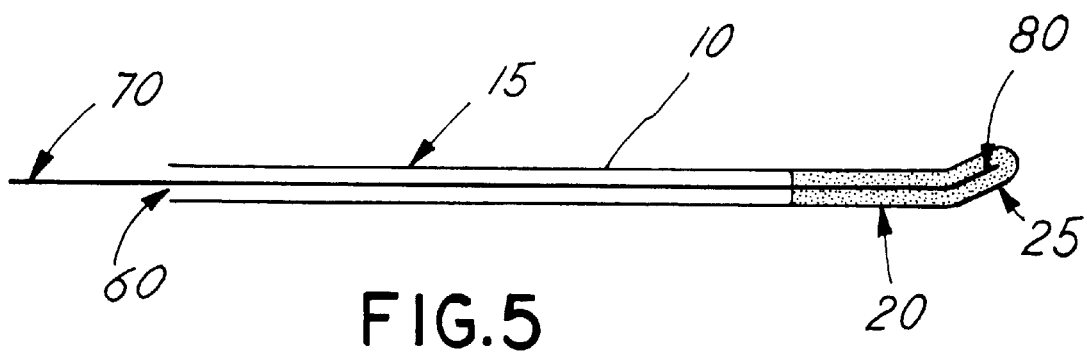
FIG. 5 is a plan view of the lead adapted to accept a stylet and having a curved distal end.

Turning to FIG. 5, the stylet 70 can alternatively have a manufactured shape. Various shapes of the stylet distal end 80 could be used to assist or guide the placement of the medical lead 10 to the optimal physiological position. An alternative shape of the stylet 70 includes a curved distal end 80. The medical lead 10 may also be manufactured with a pre-bent optimized shape to accept the stylet 70. With a pre-bent medical lead 10, a stylet 70 may or may not be used to assist in the implantation of the lead. A stylet 70 with a straight distal end 80 may be used to straighten the lead for passing through the cannula. The construction of the lead must be adapted to accommodate the stylet 70 to ensure that the stylet 70 does not rupture the insulation on the electrical conductors.

Figure 6:
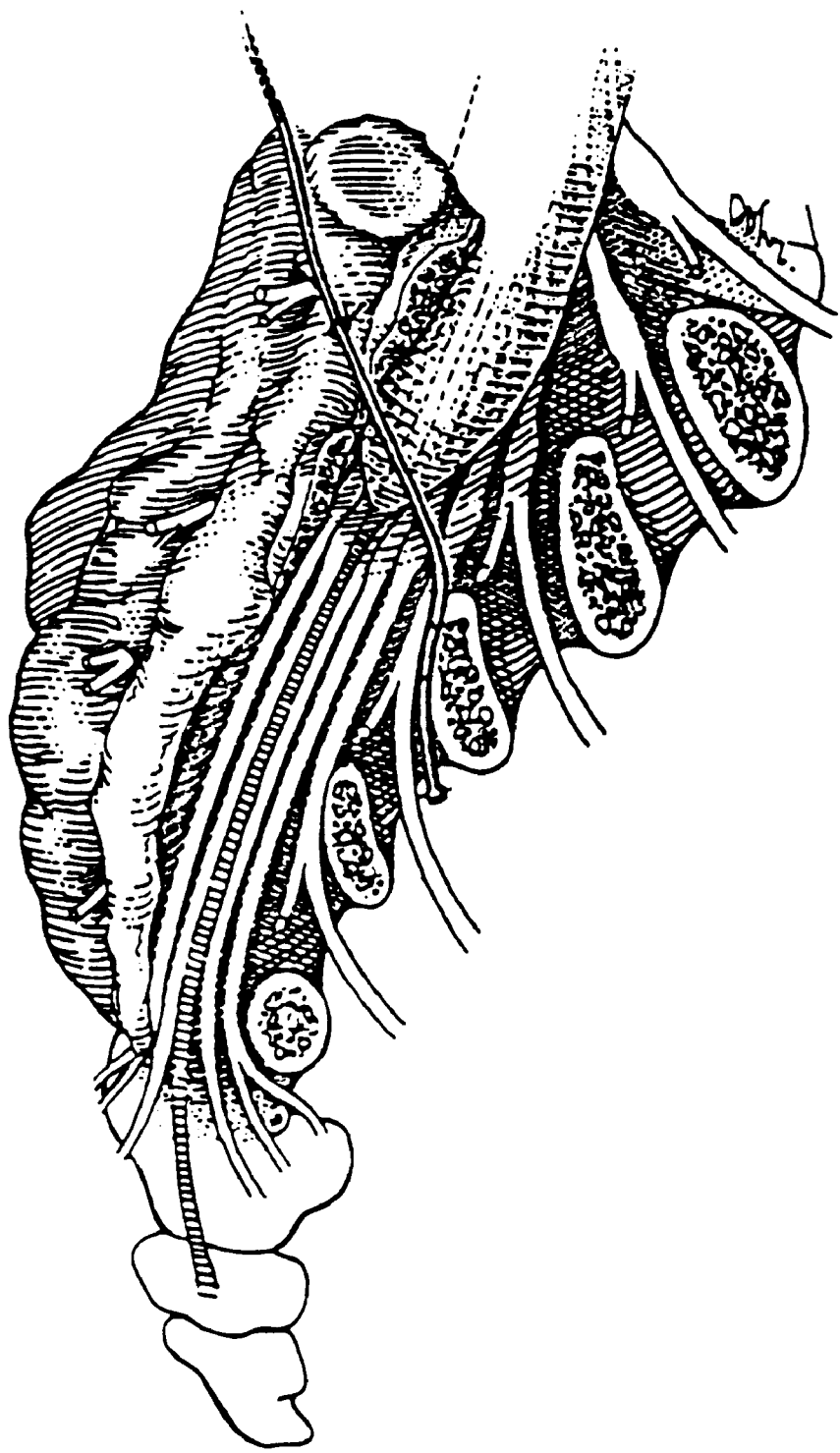
FIG. 6 is a schematic illustration of a lead implanted near the sacral nerve.

FIG. 6 shows an overall schematic of the sacral nerve area with a medical lead 10 implanted near a sacral nerve for stimulation. The implantable medical lead 10 is inserted by first making an incision appropriate to the size of the patient and then splitting the paraspinal muscle fibers to expose the sacral foramen. The physician then locates the desired position and inserts the medical lead 10 into the foramen and anchors the medical lead 10 in place. The medical lead 10 should be placed close enough to the nerve bundle that the electrical stimulation results in the desired physiological responses. The desired effect varies depending on which pelvic floor disorder is being treated or which nerve is being stimulated. The preferred position for the medical lead 10 is implantation parallel with the nerve. The parallel placement of the medical lead 10 to the nerve results in the most efficient transfer of electrical energy. With the medical lead 10 of this invention, the positioning is much less critical than current lead designs.

To determine the best location of the lead, an insulated needle with both ends exposed for electrical stimulation is used to locate the foramen and locate the proximity of the nerve by electrically stimulating the needle using an external pulse generator. The location is tested by evaluating the physiologic response and by the electrical threshold required to get that response. Once the appropriate location has been determined using the insulated needle, the medical lead 10 is implanted in that approximate location. For control of incontinence, the physician preferably implants the medical lead 10 near the S3 sacral nerves. The implantable medical lead 10 may, however, be inserted near any of the sacral nerves including the S1, S2, S3, or S4, sacral nerves depending on the necessary or desired physiologic response. This invention can be used to stimulate multiple nerves or multiple sides of a single nerve bundle. In addition, the medical lead 10 can also be used as an intramuscular lead. This may be useful in muscle stimulation such as dynamic gracilo-plasty. Placement of the medical lead 10 of this invention does not require the specificity of current electrical stimulation of the sacral nerves. Additionally, the larger electrode contacts 20 and 40 make the present invention less susceptible to migration of the implantable medical lead 10 after implantation.

The true spirit and scope of the inventions of this specification are best defined by the appended claims, to be interpreted in light of the foregoing specification. Other apparatus which incorporate modifications or changes to that which has been described herein are equally included within the scope of the following claims and equivalents thereof. Therefore, to particularly point out and distinctly claim the subject matter regarded as the invention, the following claims conclude this specification.

I claim:

1. An implantable medical lead for non-direct contact electrical stimulation of the sacral nerves, comprising, in combination:

a lead body having a distal end and a proximal end, the distal end having a first electrode contact and a second electrode contact, the first electrode contact having a length of between 0.10 inches and 1.5 inches extending longitudinally from a position at the distal end toward the proximal end, and the first electrode contact comprises a coiled wire, the second electrode contact having a length of between 0.03 to 1.00 inches, extending longitudinally from a point beyond the first electrode contact at least 1.00 inches from the distal end toward the proximal end and, the first and second electrode contact arranged and sized such that the first electrode does not longitudinally overlap with the second electrode contact, and the second electrode contact comprises a solid surface material, whereby the first and second electrode contacts of the lead body provide stimulation to the sacral nerve without necessarily being in direct contact with the sacral nerves.

2. The implantable medical lead as in claim 1, wherein the solid surface material is platinum.

3. The implantable medical lead as in claim 1, wherein the solid surface material is platinum-iridium.

4. The implantable medical lead as in claim 1, wherein the solid surface material is stainless steel.

* * * * *